United States Patent

Inoue et al.

[11] Patent Number: 5,944,740
[45] Date of Patent: Aug. 31, 1999

[54] CONDUCTIVE DEVICE TO BE APPLIED TO SKIN AND METHOD OF USE THEREOF

[75] Inventors: Hiroshi Inoue, Ikoma; Hitoshi Sakuragi, Otsu, both of Japan

[73] Assignee: Koshin International Kabushiki Kaisha, Hyogo, Japan

[21] Appl. No.: 08/884,141

[22] Filed: Jun. 27, 1997

[51] Int. Cl.$^6$ .......................................... A61N 1/04
[52] U.S. Cl. .................................................... 607/1
[58] Field of Search ............................. 607/1, 152

[56] References Cited

FOREIGN PATENT DOCUMENTS

| | | |
|---|---|---|
| 54-128195 | 10/1979 | Japan . |
| 56-37722 | 9/1981 | Japan . |
| 59-102036 | 7/1984 | Japan . |
| 60-203269 | 10/1985 | Japan . |
| 61-94039 | 6/1986 | Japan . |
| 61-240968 | 10/1986 | Japan . |
| 62-277970 | 12/1987 | Japan . |
| 864149 | 12/1990 | Japan . |
| 3-78558 | 8/1991 | Japan . |
| 4-17167 | 4/1992 | Japan . |
| 4-90357 | 8/1992 | Japan . |
| 08182767 | 7/1996 | Japan . |

*Primary Examiner*—William E. Kamm
*Attorney, Agent, or Firm*—Marshall, O'Toole, Gerstein, Murray & Borun

[57] ABSTRACT

A conductive device is applied to the skin of a subject suffering from symptoms such as musculoskeletal discomfort or pain, cold constitution, poor blood circulation, and the like, wherein a stream of charged particles is generated in the body of the subject due to the different ionization tendencies of two different types of metals employed in the conductive device.

9 Claims, 5 Drawing Sheets

CONDUCTIVE DEVICE TO BE APPLIED TO SKIN AND METHOD OF USE THEREOF

FIELD OF THE INVENTION

The present invention generally relates to a conductive device to be applied to the skin. More particularly, the present invention is directed to a conductive device to be applied to the skin of a subject suffering from symptoms such as musculoskeletal discomfort or pain, cold constitution, poor blood circulation, and the like, wherein a stream of charged particles is generated in the body of the subject due to the different ionization tendencies of two different types of metals employed in the conductive device.

BACKGROUND OF THE INVENTION

In general, conventional conductive devices for application to the skin, include those comprising two metal plates insulated from each other by an insulant disposed between them, wherein one metal plate is made from a metal having higher ionization tendency, while the other metal plate is made from a distinct metal having a lower ionization tendency.

Such a conventional conductive device is disclosed in Japanese Utility Model Application No. 57-197841 (laid open for inspection Jul. 10, 1984 and published Mar. 8, 1985). This conductive device comprises a small disk-like copper plate having a lower ionization tendency, and an aluminum ring-plate having a higher ionization tendency, which is engaged to the copper plate with a space disposed therebetween. The copper plate is disposed onto a central portion of an adhesive sheet coated with insulative adhesives. This device is further characterized in that the copper plate and the aluminum plate are provided on the adhesive surface of the adhesive sheet to avoid direct contact each other by forming a space between the two plates for insulation. When alleviation of such symptoms as musculoskeletal discomfort or pain is desired, the device is applied to a position on the skin immediately above the area of discomfort by attaching the adhesive sheet onto the skin so that the copper plate is contacted with the central area of the skin directly above the area of discomfort, while the aluminum plate is contacted with the area surrounding the central area. Thus, negatively charged particles flow into the region of discomfort in a direction from the copper plate to the aluminum plate due to the difference of the ionization tendency therebetween. The stream of charged particles produced may result in the correction of any deviation of biogalvanic electricity in the body of the subject and may exert effects to alleviate shoulder discomfort and the like via the relaxation of muscle(s), tendon(s) and the like.

In addition to the conductive device discussed above, similar effects may be expected by employing an iron plate thinly-coated with copper and an iron plate thinly-coated with aluminum-zinc, as alternatives to the combination of the copper and aluminum plates.

Although the aforementioned conductive device has been known to exert excellent effects, the thickness and total weight thereof tend to be prohibitive due to the metal plates employed. Additionally, since the space disposed between the copper plate and the aluminum plate must be maintained for insulation purposes, thickness of the aluminum plate must be larger in accordance with the width of the space. Thus, the subject may be prone to unpleasant sensations caused by such thickness and weight.

Furthermore, the elasticity of the conductive device is poor due to the metal plates employed. More specifically, when the device is applied to a non-flat or a curved portion of the body (e.g., "therapeutic point" on the fingers, or joints of the arm and the like), it is difficult to adhere the device to cover such an uneven surface. In addition, when the device is applied to such uneven surface, the user may be subject to an unpleasant sensation of a resistive force resulting from failure of the device to deform in correspondence to the movement of the "therapeutic point" or joint.

With respect to economic considerations, the per unit cost of a conventional conductive device is necessarily inflated due to the special manufacturing techniques needed with respect to the different metal plates employed therein. More specifically, when iron plates thinly-coated with copper or aluminum-zinc are employed, foundational coating with a metal such as nickel or the like is necessary for the prevention of rust prior to the thin-coat application. As a result of this necessity, the manufacture of such a conventional device is somewhat complicated and therefore costly.

SUMMARY OF THE INVENTION

The present invention has been accomplished in view of the above described problems of the conventional conductive device.

An object of the present invention is to provide a conductive device for application to the skin which exerts desirable effects to alleviate musculoskeletal discomfort or pain such as (but not limited to) shoulder discomfort, lumbar pain, general muscle strain or ache, arthritis pain, cold constitution, poor blood circulation and the like, having light weight and reasonable elasticity, so that users may not be subject to any unpleasant sensation when the device is applied to the skin. Further, the costs for manufacturing the device can be reduced to meet the commercial needs.

Therefore, one of the aspect of the present invention is to provide a conductive device for application to the skin of the subject, comprising a flexible piece and an insulative piece, said flexible piece being vapor deposited with a first metal onto at least a top surface thereof to form a first metal film, said insulative piece is vapor deposited with a second metal onto top surface thereof to form a second metal film, wherein the upper and bottom surfaces of said insulative piece have smaller areas than the upper surface of said flexible piece, and wherein said first metal has an ionization tendency which is higher than that of said second metal, and said insulative piece is fixed onto the flexible piece.

Another aspect of the present invention is to provide a device as described above, wherein the flexible piece further comprises a bulging part at the central portion thereof.

In a further aspect, the present invention provides a device as described above, with pressing protuberances, which surround the insulative piece and are disposed on the flexible piece.

Other aspects of the present invention include methods of treating musculoskeletal pain or discomfort such as (but not limited to) shoulder discomfort, lumbar pain, general muscle strain or ache, arthritis pain, cold constitution, poor blood circulation and the like and methods for producing conduction devices for treating the same.

DETAILED DESCRIPTION OF PREFERRED EMBODIMENTS

Figure 1:
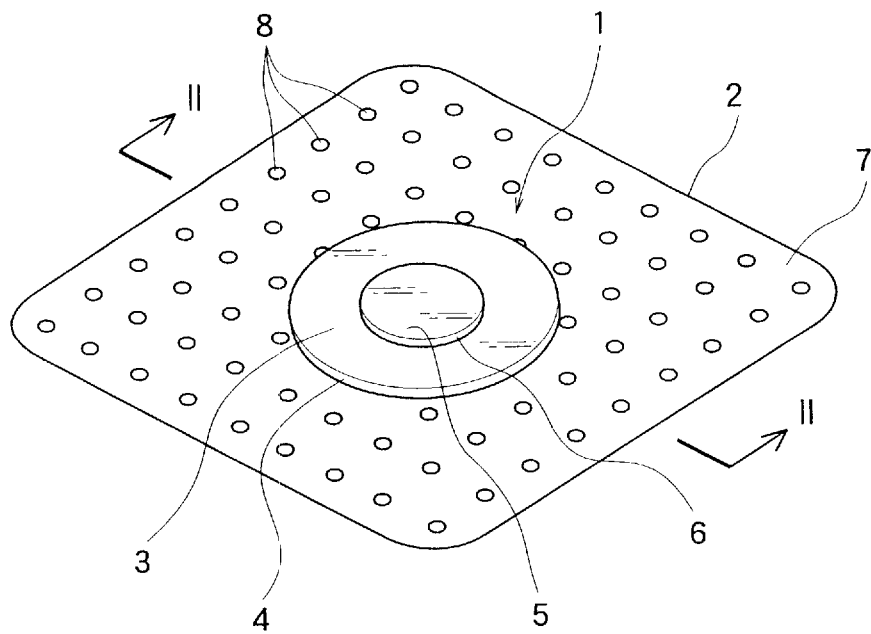
FIG. 1 is a perspective view illustrating the first embodiment of the present invention.
Figure 2:
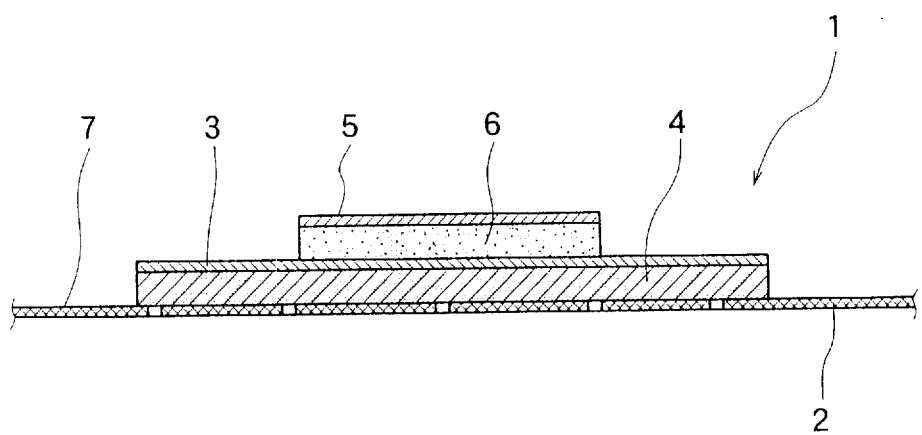
FIG. 2 is a sectional view taken substantially along line II—II in FIG. 1.

The present invention is illustrated by the following embodiments relating to conduction devices, methods of producing the same, and methods directed to the treatment of musculoskeletal pain or discomfort.

In one embodiment of the present invention, a first metal having a higher ionization tendency is vapor deposited onto at least a top surface of a flexible piece to form a first metal film, while a second metal having a lower ionization tendency than the first metal is vapor deposited onto a top surface of an insulative piece, with the upper and bottom surfaces of the insulative piece having smaller areas than the upper surface of the flexible piece.

With respect to the process for vapor deposition of the flexible piece, vacuum vapor deposition may be performed by heat-evaporating a first metal tip under highly reduced pressure and spraying the vapor of the metal onto at least a top surface (i.e., the surface to be contacted with the skin) of the flexible piece to agglutinate the vapor as a film of the first metal (first metal film). Further, a top surface of the insulative piece is also vapor deposited in a similar manner by heat-evaporating the second metal tip under highly reduced pressure to agglutinate the vapor as a film on the second metal (second metal film), wherein the ionization tendency of the second metal is lower than that of the first metal.

When the insulative piece is fixed onto the flexible piece to avoid direct contact of the first metal film with the second metal film (although both of the flexible piece and the insulative piece have acquired conductivity on their surfaces respectively), the first and second metal may be insulated from each other by the insulative piece. Thus, generation of electric current via direct contact of the two metal films will be prevented. In addition, the width of the space for maintaining a non-contacting state between the first and second metal films may correspond to the thickness of the insulative piece. Therefore, the width of the space provided to maintain a non-contacting state may be diminished by using a thinner insulative piece. Thus the entire thickness and weight of the conductive device may be reduced with a concomitant increase in flexibility.

Further, the ability of the present invention to contact more skin would be enhanced due to the increase in flexibility, while the charged particle (electron) transfer (generated when first and second metal films are attached to the skin) would be more efficient due to the reduction of the space provided to maintain a non-contacting state.

In a first embodiment, the conductive device may be applied to a position on the skin of a subject in proximity to the area of pain or discomfort (therapeutic point) using an adhesive member so that the skin may be contacted with the first metal film deposited on a top surface of the flexible piece and with the second metal film deposited on a top surface of the insulative piece. Under such a state, the first metal having a higher ionization tendency may emit a large number of electrons due to its high cationization potency. Therefore, negative charge may be imparted to the area surrounding the central area of the position on the skin surface where the first metal film is contacted. When such a surface of the skin gains negative charge in this manner, the region under the area surrounding the central area of the skin position may gain positive charge through electrostatic induction. With respect to the central area contacting with the second metal having a lower ionization tendency, the surface thereof may gain a relatively positive charge, thereby a negative charge may be imparted to the region under this central area. As a result, in the region under the position on the skin where the two metal films have been attached, anions will flow in a direction from the central area, which is opposed to the second metal film on the insulative piece, to the peripheral area, which is opposed to the first metal film on the flexible piece. Consequently, the stream of charged particles generated would change bioelectricity in the body of the subject.

In a second embodiment of the present invention, the flexible piece further comprises a bulging part having a spring means at the central portion of the piece. Thus, when the device is applied to the skin of a subject in proximity to the area of pain or discomfort using an adhesive member similar to that of aforementioned first embodiment, the insulative piece may continuously press the surface of the skin due to the elasticity of the bulging part imparted by the spring means. Accordingly, in addition to the above-described effects resulting from the stream of charged particles generated, acupressure effects may also be expected through the bulging or returning spring-like movement of the bulging part in accordance with the movement of the muscle or the like.

Further, according to a third embodiment of the present invention, at least one pressing protuberance surrounding the insulative piece, is disposed on the flexible piece. Therefore, when the device is applied to the skin of a subject in proximity to the area of pain or discomfort using an adhesive member as described above, the pressing protuberances will press the skin, thereby causing acupressure effects to the affected area of the subject via a stimulative pressing force. Additionally, when the flexible piece further comprises a bulging part having a spring-like function at the central portion as described above (second embodiment), the insulative piece may continuously press the surface of the skin due to the elasticity of the bulging part with the acupressure effects further improved by the pressing protuberances.

EXAMPLE

FIGS. 1 through 10 illustrate the conductive device 1 with an adhesive member 2 having an adhesive surface 7 therewith. The adhesive member 2 (e.g., see FIG. 1, which is illustrated in the Figures, is an adhesive sheet of a substantially square form having pores 8 distributed over the sheet to increase air permeability of the adhesive member 2.

A conductive device 1 of the present invention may be applied to skin so that it may be contacted with and retained onto position "a" (affected portion) of the skin of the subject "A" (e.g., see FIGS. 3 and 4 ) using an adhesive member 2 as shown in FIGS. 1–5. The device 1 comprises a flexible piece 4 and an insulative piece 6, wherein the flexible piece 4 is vapor deposited with a first metal onto at least a top surface thereof to form a first metal film 3, and wherein the insulative piece 6 is vapor deposited with a second metal onto top surface thereof to form a second metal film 5. The ionization tendency of the first metal 3 is higher than that of the second metal 5, and the areas of the upper and bottom surfaces of the insulative piece 6 are smaller than that of the upper surface of the flexible piece 4. The insulative piece 6 is fixed onto the flexible piece 4 to avoid direct contact of the first metal film 3 with the second metal film 5.

The adhesive member 2 may be employed for attaching and maintaining the flexible piece 4 and the insulative piece 6 on to position "a" of the skin of subject "A" or to any other desired position on a subject. This adhesive member 2 may be any means for adhering the conductive device, however, preferred for example is soft sheet material, which can be bent freely, such as thin cloth or synthetic resin papers. An adhesive surface 7 may be provided by coating adhesives to one surface of the adhesive member 2 so as to be attachable to and detachable from the skin. In a preferred embodiment, the adhesive member 2 may be court plaster. However, bandages, supporters, and the like may also be useful as the adhesive member 2. Further, the adhesive member 2 may be of any material or form as long as it is able to secure the flexible piece 4 and the insulative piece 6 to a position, for example position "a," on the skin of subject "A" (e.g., see FIGS. 3 and 4). Preferably the adhesive member should not cause an uncomfortable sensation for the subject when it is applied to the skin.

The color of the adhesive member 2 may be any color however, preferred colors are selected from a variety of flesh colors so as to be indistinguishable from the skin. When a light permeable substance is incorporated into the adhesive member 2, bioactivities of the affected part of the subject's body (attached to the adhesive member 2) may be advantageously maintained because incident light will be allowed to pass through to position "a" without blockade.

Figure 6:
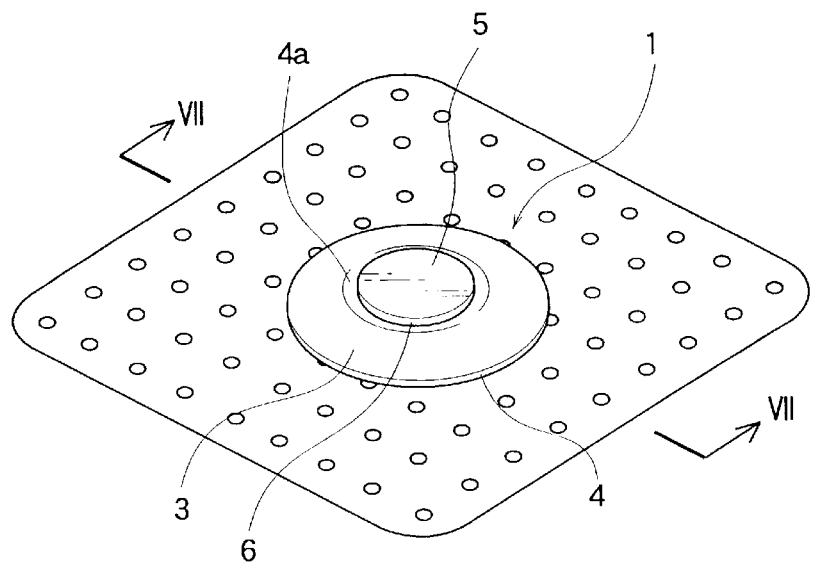
FIG. 6 is a perspective view illustrating the second embodiment of the present invention.

The aforementioned flexible piece 4 may be made of a thin type of a synthetic resin having elasticity (e.g., as polyester) to form a disk-like shape (e.g., see FIGS. 1 and 6). The material of the flexible piece 4 may be any material so long as it has appropriate elasticity and feasibility to be vapor deposited with the first metal.

The thickness of the flexible piece 4 generally ranges from 30 $\mu$m to 300 $\mu$m and more preferably from 50 $\mu$m to 200 $\mu$m. The shape of the flexible piece 4 may be circular or elliptical or it may be a polygon such as square, rectangle, hexagon or the like.

The flexible piece 4 may be made obtain conductive by vapor deposition of the first metal (e.g., aluminum) onto at least a top surface of the piece, to form the first metal film 3 having a relatively higher ionization tendency. A preferred thickness of the first metal film 3 is approximately 300 Å, but may be any thickness. Also, the flexible piece 4, having the first metal film 3 deposited thereon, may be thinner and lighter than described above, thereby increasing the elasticity of the flexible piece 4.

The insulative piece 6 may be a thin tip made of a synthetic resin, such as polyester, (or any material that has appropriate insulative properties) with the areas of the upper and bottom surfaces of the insulative piece 6 being smaller than that of the upper surface of the flexible piece 4 (e.g., see FIGS. 2, 5, 7, 8, and 10). The insulative piece 6 may also be formed from an insulative material such as ceramic, glass or the like or from a thin piece of any material wherein the bottom surface thereof may be coated with insulatives to impart satisfactory insulation efficacy. The form of the insulative piece 6 may also be a small disk. The thickness of the insulative piece 6 generally ranges from 30 $\mu$m to 300 $\mu$m and more preferably, from 50 $\mu$m to 200 $\mu$m. A preferred shape of the insulative piece 6 may be (but not limited to) circular or elliptical or it may be a polygon such as a square, rectangle, hexagon or the like.

Conductivity of the top surface of the insulative piece 6 is provided by vapor depositing the second metal to form the second metal film 5 as described above for the flexible piece 4. The second metal, (e.g., platinum or gold) would have an ionization tendency lower than that of the first metal. The thickness of the second metal film 5 is approximately but not limited to 300 Å. Further, in view of the economical considerations, the second metal film 5 may be thinner when a noble metal is employed. Also, the insulative piece 6 deposited with the second metal film 5 may be the thinner and lighter thereby increasing the elasticity of the insulative piece.

The flexible piece 4 and the insulative piece 6 thus form a multi-layer structure (e.g., see FIGS. 2, 5, 7, 8, and 10), wherein the bottom surface of the flexible piece 4 is affixed to the central portion of the adhesive surface 7 of the adhesive member 2, and the bottom surface of the insulative piece 6 is fixed tightly to the central portion of the first metal film 3 on the flexible piece 4 by an adhesive (e.g., epoxy type adhesives and the like). In this embodiment, the insulative piece 6 and the adhesives employed (to fix the insulative piece 6) play a role in insulation. Namely, the insulative piece 6 and the adhesives intervene between the first metal film 3 on the flexible piece 4 and the second metal film 5 on the insulative piece 6 for insulation (see, FIGS. 1 and 2).

The combination of the first metal on the flexible piece 4 and the second metal on the insulative piece 6 may be aluminum-gold or platinum as described above. In addition, various combinations of the metals may also be used, e.g., aluminum-copper, aluminum-silver, zinc-gold, zinc-silver or the like, so long as the metals differ in ionization tendency.

The above-described conductive device 1 may be applied to for example position "a" on the skin of subject "A" in order to alleviate musculoskeletal discomfort or pain such as (but no limited to) shoulder discomfort, lumbar pain, general muscle strain or ache, arthritis pain, cold constitution, poor blood circulation and the like. When the device 1 is applied to position "a," the second metal film 5 on the insulative piece 6 is contacted with the central area of the skin of position "a," while the first metal film 3 on the flexible piece 4 may be contacted with the area surrounding the central area of the position "a" by attaching the adhesive surface 7 of the adhesive member 2 to position "a" of the skin of subject "A."

Thus, a large number of electrons may be emitted from the first metal film 3 on the flexible piece 4, thereby allowing the surface opposed to the area surrounding the central area of the position "a" contacting with the first metal film 3 to gain a negative charge. When the surface of the surrounding area gains a negative charge in such a manner, the region of subject "A's" body under the surrounding area may gain positive charge through electrostatic induction. With respect to the area contacting with the second metal film 5 on the insulative piece 6, the opposed skin surface gains a relatively positive charge, thus the region under the skin surface gains a negative charge. Accordingly, the negative ions flow in the region under position "a" in a direction from the central area (of which surface is contacted with the second metal film 5) to the peripheral area (of which surface is contacted with the first metal film 3). The stream of charged particles generated may result in correction of any deviation of bioelectricity in the body of the subject, thereby leading to an alleviation or cure of musculoskeletal discomfort or pain such as but not limited to shoulder discomfort, lumbar pain, general muscle strain or ache, arthritis pain, cold constitution, poor blood circulation and the like via relaxation of muscle(s), tendon(s) and the like.

Furthermore, since the metal films have been made from fine particles of metal, the reflection efficacy of infrared radiation from the position "a" of the skin is improved, thereby enhancing the effects of the device 1 through reflection of infrared radiation into the affected portion of the subject's body. This is especially true and may be expected when the second metal film 5 is vapor deposited gold.

Figure 3:
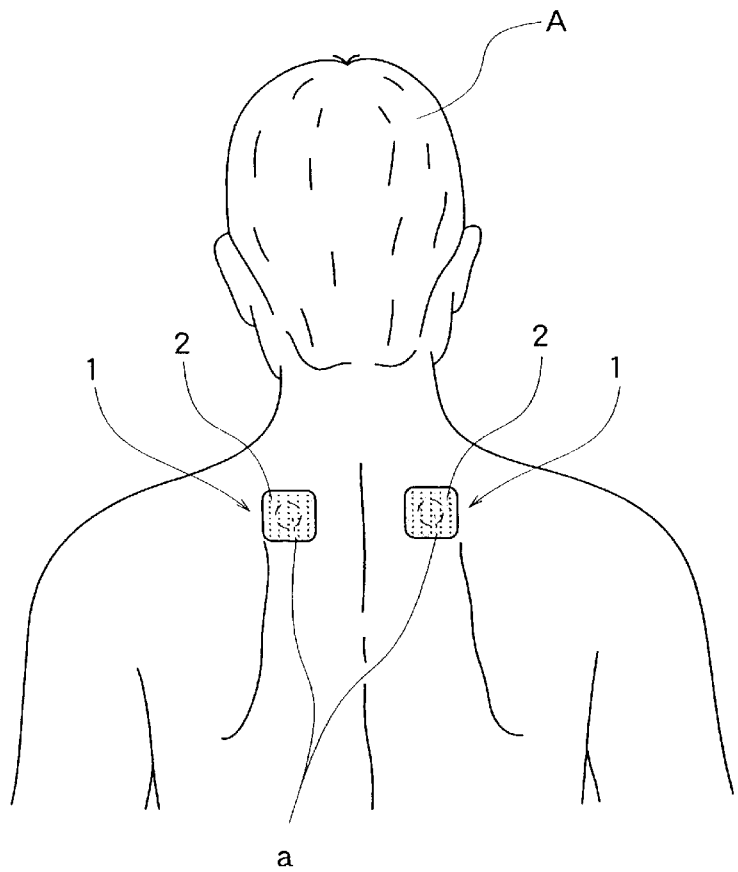
FIG. 3 is a schematic view illustrating a mode utilizing the first embodiment of the present invention.
Figure 4:
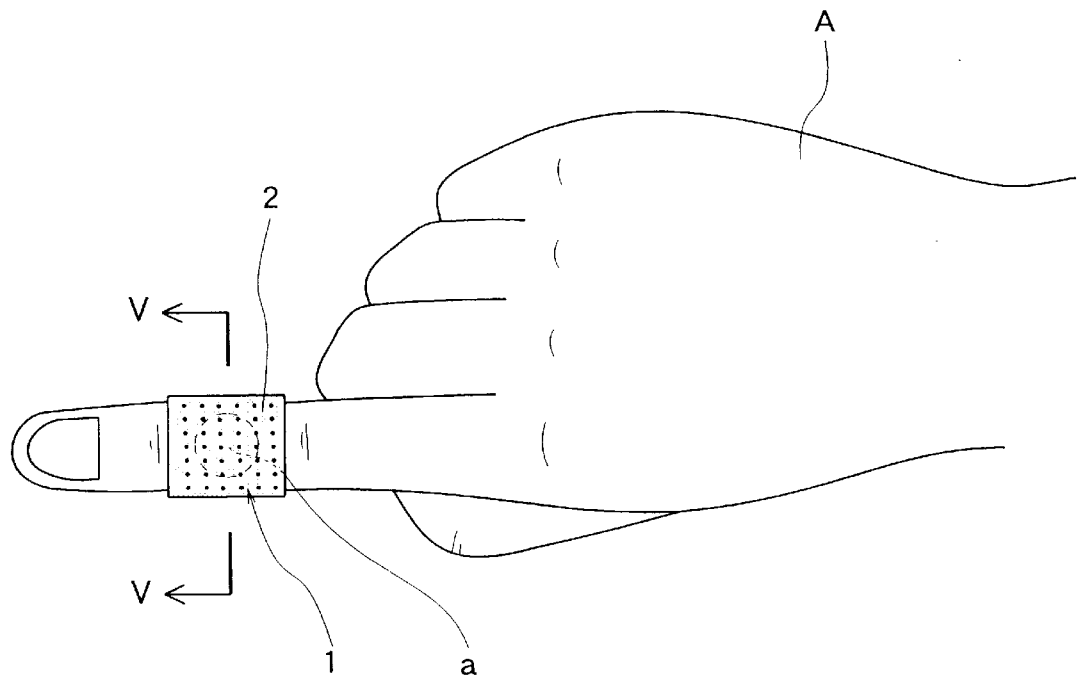
FIG. 4 is a schematic view illustrating another mode utilizing the first embodiment of the present invention.
Figure 5:
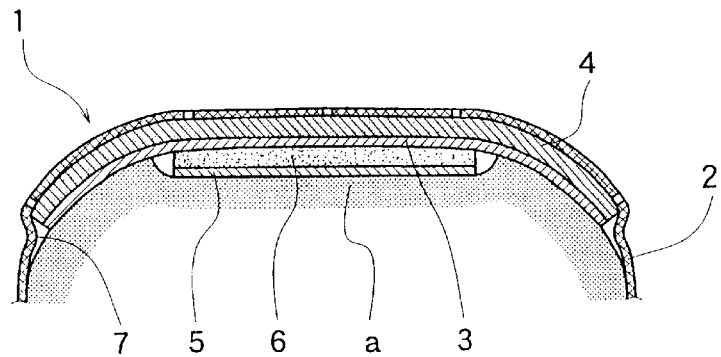
FIG. 5 is a partial sectional view taken along line V—V in FIG. 4.

Moreover, because the conductive device 1 is elastic or flexible by virtue of the flexible piece 4, the device may be applied readily onto a narrow and/or curved surface, such as fingers, where attaching of such devices has normally been difficult (e.g., see FIGS. 3–5). When the device 1 of the present invention is applied to such a location, similar effects described above may also be expected. More specifically, contact of the second metal film 5 on the insulative piece 6 with the central area of position "a" wherein position "a" is a finger of subject "A", concomitant and secure cohesion of the first metal film 3 onto the area surrounding the central area of the position "a" is achieved through deformation or bending of the flexible piece 4 in correspondence with the curved surface of the skin.

Figure 7:
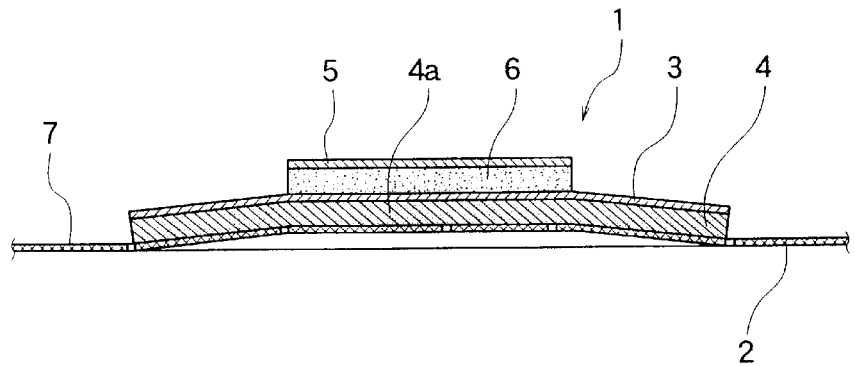
FIG. 7 is a schematic transverse sectional view of the second embodiment of the present invention taken along line VII—VII in FIG. 6.
Figure 8:
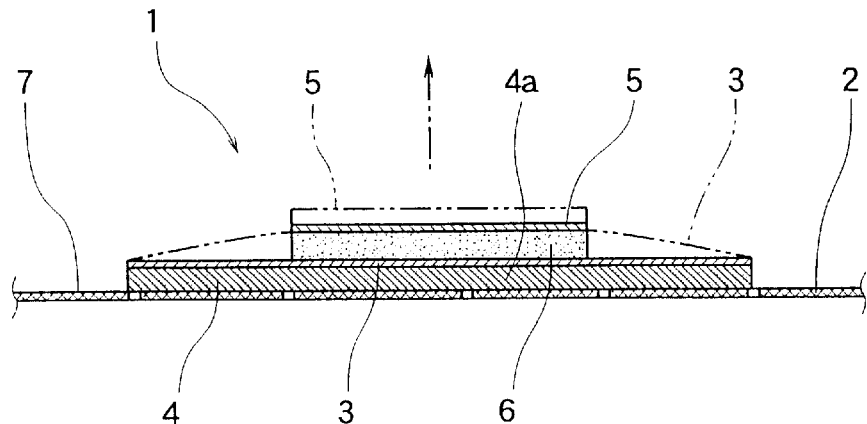
FIG. 8 is a schematic transverse sectional view of the second embodiment of the present invention to explain an operation mode taken along line VII—VII in FIG. 6.

Another embodiment of the present invention is shown in FIGS. 6–8. The flexible piece 4 of the conductive device 1 further comprises a bulging part 4a having a spring-like function at the central portion thereof, wherein the bulging part 4a is movable upon receiving pressure in a perpendicular direction to the surface of the flexible piece 4. When the conductive device 1, comprising the flexible piece 4 having a bulging part 4a, is applied to position "a" on the skin of subject "A," the spring-like function of the bulging part 4a will work in accordance with the movement of the muscle(s) or tendon(s). Thus, the second metal film 5 on the insulative piece 6 may be kept in a state such that it presses against the central area of position "a" with a variable force. Therefore, an action similar to that of acupressure may continuously be exerted against position "a" thereby resulting in an effect similar to that caused by acupressure.

Figure 9:
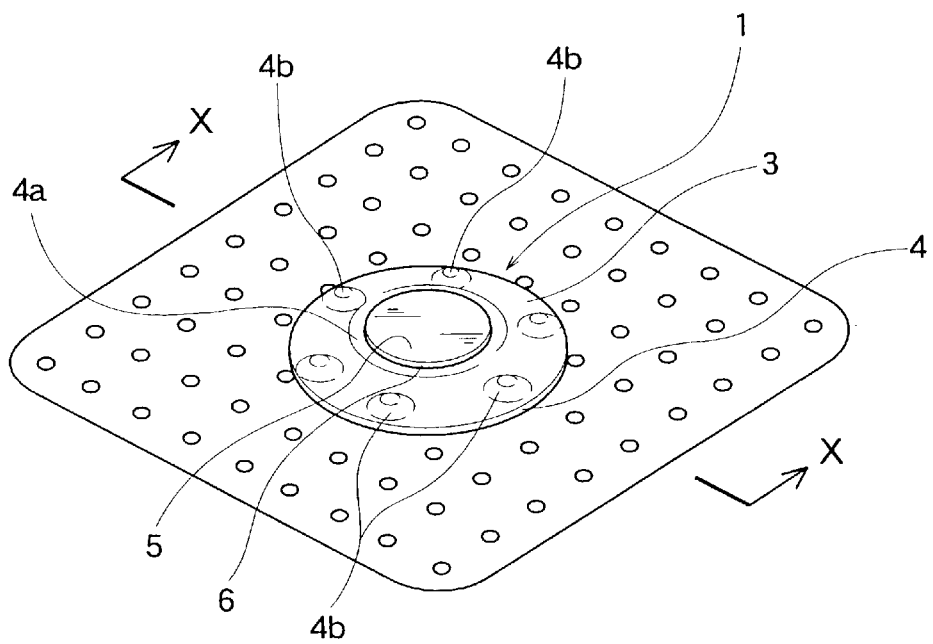
FIG. 9 is a perspective view illustrating the third embodiment of the present invention.
Figure 10:
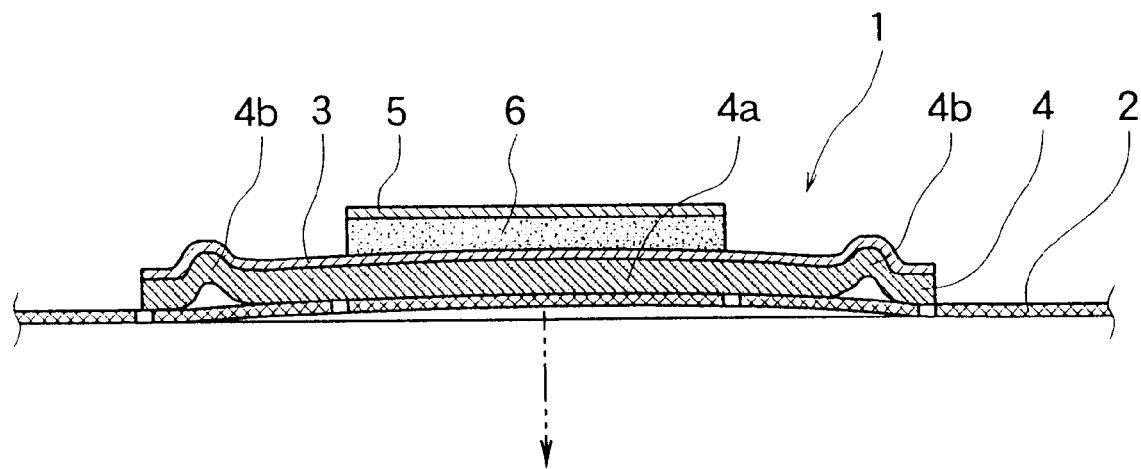
FIG. 10 is a schematic transverse sectional view of the third embodiment of the present invention taken along line X—X in FIG. 9.

The conductive device 1 shown in FIGS. 9–10 is another embodiment wherein the flexible piece 4 comprises a bulging part 4a having a spring-like function (achievable with spring means) at the central portion thereof as above described, and at least one pressing protuberance 4b surrounding the insulative piece 6 and disposed on the flexible piece 4. When the device 1, comprising such a flexible piece 4, is applied for example to position "a" on the skin of the subject "A," the second metal film 5 of the insulative piece 6 is kept in a state such that it may press the central area of position "a" with a variable force by means of a spring-like function resulting from the bulging part 4a in accordance with the movement of the muscle. Furthermore, the pressing protuberances 4b on the flexible piece 4 may be embedded into the area surrounding the central area of the position "a". Consequently, effects similar to those of acupressure may be expected to the position "a" via the pressing stimuli from the protuberances 4b.

As still another embodiment of the present invention, the conductive device 1 may comprise the flexible piece 4 with at least one pressing protuberance 4b surrounding the insulative piece 6 disposed on the flexible piece 4 to obtain the similar effects to the acupressure-like effect without the bulging part 4a.

Finally in all the aforementioned embodiments, it is advantageous to construct the device to be as thin as possible thereby causing the device to be lighter and more elastic. Such properties (1) will reduce any unpleasant sensation to the subject, (2) will further allow the user to apply the device to a curved or uneven surface of the skin, and (3) will reduce the cost of the device due to the reduction in the amount of metal to be used. Still further in all the aforementioned embodiments, it is advantageous to vapor deposit the metal film so as to increase the reflection efficacy of the infrared radiation.

In the second preferred embodiment of the present invention in conjunction with the advantages described directly above, it is further advantageous to have a flexible piece comprising a bulging part, which itself has a spring-like function at the central portion thereof (i.e., to cause acupressure to affected portion of subject's body).

In conjunction with the advantages described directly above, it is yet a further advantage to have at least one pressing protuberance surrounding the insulative piece, which are disposed on the flexible piece (i.e., to cause additional acupressure effects)

Although the present invention has been described in types of preferred embodiments, it is intended that the present invention encompass all modifications and variations which occur to those skilled in the art upon consideration of the disclosure herein, and in particular those embodiments which are within the broadest proper interpretation of the claims and their requirements.

What is claimed is:

1. A conductive device to be applied to skin of the subject comprising:

a flexible piece having a top surface and a lower surface;

a first metal vapor-deposited on the top surface of the flexible to form a first metal film;

an insulative piece having an upper surface and a bottom surface; and a second metal vapor-deposited on the upper surface of the insulative piece to form a second metal film, wherein the bottom surface of the insulative piece is fixed upon the top surface of the flexible piece, and wherein the upper and bottom surfaces of the insulative piece have smaller areas than the upper surface of the flexible piece, and wherein the first metal has an ionization tendency that is higher than the ionization tendency of the second metal.

2. The conductive device of claim 1 wherein the first metal and the second metal are chosen from the group of combinations consisting of aluminum-gold, aluminum-platinum, aluminum-copper, aluminum-silver, zinc-gold, and zinc-silver.

3. The conductive device of claim 1 further comprising an adhesive member, wherein the conductive device is attached to the skin of a subject by the adhesive member.

4. The conductive device according to claim 3 wherein said adhesive member is chosen from the group consisting of synthetic resin papers, bandages, and court plaster.

5. The conductive device of claim 1 wherein said insulative piece comprises synthetic resin.

6. The conductive device according to claim 5 wherein said insulative piece comprises polyester.

7. The conductive device of claim 1 wherein said flexible piece comprises synthetic resin.

8. The conductive device according to claim 7 wherein said flexible piece comprises polyester.

9. A method of treating musculoskeletal pain or discomfort comprising:

(a) providing the conductive device as in any of claims 1 and 2–8 to an individual having musculoskeletal pain or discomfort; and (b) applying the conductive device to the individual's skin in proximity to the area of pain or discomfort.

* * * * *